United States Patent
Hoic et al.

(10) Patent No.: US 6,669,930 B1
(45) Date of Patent: Dec. 30, 2003

(54) LIQUID TOOTH WHITENING GEL

(75) Inventors: Diego A. Hoic, Highland Park, NJ (US); Jobiah Sabelko, Princeton, NJ (US); Prakasarao Mandadi, Hillsborough, NJ (US); Suryakant Patel, Bridgewater, NJ (US); Nagaraj Dixit, Plainsboro, NJ (US); Michael Prencipe, West Windsor, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 10/342,076

(22) Filed: Jan. 15, 2003

(51) Int. Cl.[7] .............................. A61K 7/16; A61K 7/20
(52) U.S. Cl. ........................... 424/49; 424/53; 433/215; 433/216
(58) Field of Search ............................... 424/53; 433/45, 433/216

(56) References Cited

U.S. PATENT DOCUMENTS

| | | | | |
|---|---|---|---|---|
| 3,711,604 A | * | 1/1973 | Colodnoy et al. | 424/52 |
| 3,934,000 A | * | 1/1976 | Barth | 424/47 |
| 3,944,661 A | * | 3/1976 | Colodnoy et al. | 424/49 |
| 3,954,961 A | * | 5/1976 | Colodny et al. | 424/49 |
| 3,957,968 A | * | 5/1976 | Cordon | 424/57 |
| 4,075,316 A | * | 2/1978 | Cordon | 424/49 |
| 4,433,091 A | * | 2/1984 | Poulsen | 524/386 |
| 4,792,357 A | * | 12/1988 | Bier | 106/600 |
| 4,849,212 A | * | 7/1989 | Glandorf et al. | 424/52 |
| 5,985,258 A | * | 11/1999 | Alwattari et al. | 424/70.7 |
| 6,447,757 B1 | * | 9/2002 | Orlowski et al. | 424/53 |
| 6,565,979 B1 | * | 5/2003 | Bosch et al. | 428/423.1 |
| 6,569,408 B1 | * | 5/2003 | Yue et al. | 424/49 |

FOREIGN PATENT DOCUMENTS

| CA | 982946 | * | 2/1976 |
|---|---|---|---|

OTHER PUBLICATIONS

Colgate Simply White Trademark application 78 121948 Apr. 16, 2002 Dentiprice Toothpaste Bleaching Preparation.*

Colgate Simply White Trademark application 75983041 Jan. 20, 1999 Tooth Whitening Toothpaste.*

Brian Wilk Simply White Tooth Whitener Dental Bleaching Trademark application 75624163 Jan. 20, 1999.*

Colgate Simply White Clear Whitening Gel and Simply White Night Clear Whitening Gel www.colgatesimplywhite.com, Jul. 2003.*

* cited by examiner

*Primary Examiner*—Shep K. Rose
(74) *Attorney, Agent, or Firm*—Bernard Lieberman

(57) ABSTRACT

A storage stable liquid peroxide whitening gel composition opacified with an organic and inorganic particles.

12 Claims, No Drawings

LIQUID TOOTH WHITENING GEL

BACKGROUND OF THE INVENTION

1. Field of the Invention

This invention relates in general to tooth whitening liquid gels and more particularly to a stable, aqueous, peroxide-containing liquid gel whitening product useful for whitening tooth enamel.

2. The Prior Art

It has become desirable for a person's teeth to appear bright or "white". Society places a high value on the "whiteness" of one's teeth. One whose teeth are white may enjoy more personal confidence and satisfaction and may even enjoy greater social acceptance.

A tooth is comprised of an inner dentin layer and an outer hard enamel layer that is the protective layer of the tooth. The enamel layer of a tooth is naturally an opaque white or slightly off-white ("ivory") color. It is the enamel and dentin layers that can become stained or discolored. The enamel layer of a tooth is composed of hydroxyapatite mineral crystals that create a somewhat porous surface. These hydroxyapatite crystals form microscopic hexagonal rods or prisms that make up the enamel surface. As a result, the surface of the enamel layer presents microscopic spaces or pores between the prisms. It is believed that this porous nature of the enamel layer is what allows staining agents and discoloring substances to permeate the enamel and discolor the tooth. These remaining substances can occupy the microscopic spaces and eventually alter the color of the tooth.

Many substances that a person confronts or comes in contact with on a daily basis can "stain" or reduce the "whiteness" of one's teeth. In particular, the foods, tobacco products and fluids that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth. So long as the discolored teeth are still healthy and do not pose any health risk or problem, a product or substance that would whiten the discolored teeth would be advantageous.

It is also essential that a tooth whitening product that is to be used at home or in private by the consumer be safe and easy to use and be stable and retain its whitening efficacy during its storage on retail store shelves as well as over the period of use by the consumer.

Products and substances that are presently available to whiten teeth include a variety of different ingredients, but the primary active ingredient is a peroxide containing agent formulated into a liquid, solution, paste or gel. These products upon storage lose their whitening efficacy over time. A further limitation of commonly used aqueous peroxide solutions, is their brief period of efficacy when applied to the teeth in the oral cavity. For example, saliva, contains high concentrations of the enzyme catalase, which on contact, rapidly decomposes the peroxide into gaseous oxygen and water and so that there is only transitory contact of the peroxide whitening agent with the teeth. In addition, the low viscosities of aqueous peroxide solutions do not allow the peroxide whitening agent to remain in contact with the teeth for as long as is necessary to effect substantive whitening because of the constant flushing effects of salivary secretions. This tendency toward rapid decomposition of peroxide and the rapid flushing away of the peroxide agent applied to the teeth has severely limited their application to, and utility for, whitening teeth. It would be highly desirable, therefore, to provide a stable peroxide whitening liquid having increased retention on teeth to effect substantive whitening.

In copending U.S. patent application Ser. No. 10/155,496 filed May 24, 2002 there is disclosed a liquid gel dental whitening composition containing a peroxide whitening constituent dispersed in an aqueous liquid vehicle in which is dispersed a film forming component, the liquid gel rapidly drying when applied to the tooth surfaces to form in situ a gel-like film containing the peroxide whitening agent.

In one embodiment of the invention disclosed in U.S. Ser. No. 10/155,496 there is provided an aqueous tooth whitening liquid gel having enhanced stability and whitening efficacy, the liquid gel being comprised of an aqueous vehicle containing a film forming combination of an ethylene oxide linear homopolymer, a Carbomer and a peroxide whitening agent, the pH of the composition being maintained at an acidic level.

The whitening liquid gel of U.S. Ser. No. 10/155,496 is a portable oral care tooth whitener that can be conveniently painted onto the tooth surface. Upon the paint-on application to the teeth, the applied liquid whitening composition rapidly dries to produce, in situ, an adherent film of a thick gel that has the capacity to release the peroxide whitening agent over an extended period of time. The film adheres to the tooth surface whereby the released peroxide source then whitens the teeth to which the film is applied, the film being sufficiently adherent to counteract the tooth flushing action of saliva generated in the oral cavity. The adjustment and maintenance of the composition pH to acid levels provides a peroxide source that is stable to decomposition on storage.

A problem encountered in the use of the liquid whitening gel of U.S. Ser. No. 10/155,496 is that the composition is a clear, colorless product and the user when applying the product to tooth surfaces is uncertain, because of the product transparency, whether or not the tooth surfaces selected for whitening have had applied thereto the complete required application of the product. Less than complete application of the product to tooth surfaces can result in incomplete or reduced whitening results.

Attempts to opacify the clear product with opaque pigments particles encounter the problem that such opacifiers when present in the liquid whitening gel have been found to be interactive with, and decompose, the peroxide ingredient with the result that the whitening efficacy of the gel is reduced, providing undesirable uneven tooth whitening.

SUMMARY OF THE INVENTION

In accordance with the present invention there is provided a stable, opaque liquid whitening gel which can be visualized by the user after application to tooth surfaces which gel comprises a peroxide containing whitening agent dispersed in an orally acceptable vehicle comprising a film forming ingredient and opacifying particles selected from polymer particles, titanium oxide and titanium dioxide coated mica particles, the peroxide containing whitening agent being substantially stable in the presence of the opacifying particles.

DESCRIPTION OF THE PREFERRED EMBODIMENTS

The vehicle used to prepare the liquid gel whitening composition of the present invention preferably includes a non-toxic volatile alcohol or any suitable mixture thereof. The presence of the volatile alcohol imparts a rapid drying property to the applied liquid gel whitening composition and is present in the composition at a concentration of about 10 to about 50% by weight and preferably about 25 to about 40% by weight. A monohydric alcohol such as ethanol is preferred as a volatile solvent. Water is included in the vehicle of the composition and about 5 to about 30% by weight of the composition and preferably about 10 to about 20% by weight.

The proportion of vehicle used to prepare the liquid gel composition of the present invention is generally within the range of about 40 to about 80% by weight of the invention and preferably about 40 to about 60% by weight of the composition. A humectant such as sorbitol, glycerin propylene glycol, PEG 600 is present in the vehicle of the present invention at a concentration of about 2 to about 15% by weight and preferably about 3 to about 8 by weight.

Examples of poly(ethylene oxides) useful in the practice of the present invention include PEG 2M, 5M, 7M, 14M, 23M, 45M and 90M commercially available from Union Carbide, Danbury, Conn., ranging in molecular weight from 100,000 to 4 million. A poly(ethylene oxide) preferred for use in the practice of the present invention is a poly(ethylene oxide) having a molecular weight of about 100,000. Such poly(ethylene oxide) or PEG 2M is a nonionic polymer of ethylene oxide having an average molecular weight of 100,000 and has the general formula:

wherein n represents the number of repeating $CH_2CH_2O$ groups.

Film forming agents useful in the practice of the present invention include Carbomers such as carboxymethylene polymers including acrylic acid polymers, and acrylic acid copolymers. Carboxypolymethylene is a slightly acidic vinyl polymer with active carboxyl groups. A carboxypolymethylene preferred for use in the practice of the present invention is a water dispersible copolymer of acrylic acid cross-linked with approximately 0.75% to approximately 1.5% polyallyl sucrose that is sold under the trade designation Carbopol 934 or 974 by B.F. Goodrich. The Carbopol product is present in the liquid whitening composition of the present invention at a concentration of about 0.25 to about 1.5% by weight and preferably about 0.5 to about 1.0% by weight.

Peroxide containing compounds which may be used as whitening agents in the practice of the present invention include hydrogen peroxide, urea peroxide and percarbonate salts such as sodium percarbonate persulfate salts such as sodium persulfate and perborate salts such as sodium perborate. Most preferred is hydrogen peroxide. The peroxide containing compound is present in the liquid whitening gel compositions of the present invention at a concentration that will provide about 0.3 to about 12% by weight and preferably about 1 to about 10% by weight, active peroxide to the whitening gel formulation.

At the acid pH levels at which the composition of the present invention is maintained the Carbomer of the Carbopol type behaves like a liquid gel rather than a solid gel so that the Carbomer in combination with the poly(ethylene oxide) constituent provides thickness to the liquid product while maintaining a suitable consistency enabling the product to be painted on the tooth surface with a soft applicator brush.

Polymeric opacifying particles useful in the practice of the present invention include olefin and fluoro polymers that may be incorporated in the liquid gel whitening compositions of the present invention which are unreactive with peroxide whitening agents present in the gel, and the gel once applied to the teeth forms a thin continuous film which can be visualized by the user, such polymers including polyethylene, polypropylene and ethylene/proylene copolymers, polytetrafluoro-ethylene and polyhexafluoropropene. The opacifying polymers are incorporated in the liquid gel as powders having an average particle size in the range of about 0.5 to about 100 microns and preferably from about 1 micron to about 20 microns. Olefin polymers preferred in the practice of the present invention are polyethylene and polypropylene powders. Such powders are available from Micropowders, Inc. under the trade designation Micropoly 220 (polyethylene), Whitepoly 50, Microslip 519 (polytetrafluoroethylene). The polymeric opacifying particles are incorporated in the liquid whitening gel compositions of the present invention at concentrations of about 1 to about 30% by weight and preferably about 3 to about 9% by weight without affecting the stability of the peroxide whitening agent present in the liquid whitening gel.

Titanium dioxide and titanium dioxide coated mica particles having an average particle size range of about 0.5 to about 75 microns and preferably about 5 to about 60 microns are also useful opacifying agents in liquid whitening gel of the present invention except that the concentration of these particles in the gel composition are used in the range of up to 1.0%, and preferably between 0.15% to 1.0% by weight. Higher concentration levels of the titanium dioxide and titanium dioxide coated mica particles have tendency to destabilize the peroxide whitening agent during storage of the liquid whitening gel.

The liquid whitening gel composition of the present invention may also contain a flavoring agent. Flavoring agents that are used in the practice of the present invention include natural or synthetic essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen. The flavoring agent is incorporated in the whitening liquid composition of the present invention at a concentration of about 0.1 to about 2% by weight and preferably about 0.1 to about 0.5% by weight.

The liquid gel whitening composition of the present invention is initially prepared in the form of a liquid varnish and applied as such to the users teeth as by painting the teeth with a soft applicator. After application by the user, the alcohol and water vehicle constituents rapidly evaporate to leave a film or coating of a thick liquid gel on the teeth to which the varnish has been applied. The deposited film is comprised of the poly(ethylene oxide) constituent, the Carbomer constituent, the opacifier and the peroxide whitening agent or agents. The presence of the poly(ethylene oxide) and Carbomer constituent combination permits a slow release of the peroxide agent or agents to the applied tooth site, providing prolonged whitening treatment of the site.

The deposited film of liquid gel contains no ingredients imparting thereto an unacceptable taste or texture, rendering it unpleasant to the user and adheres strongly to tooth enamel. After application to the teeth, the composition dries in a relatively short time period, for example, 20 to 60 seconds to yield a strongly adherent, even layered opaque film which can be easily visualized by the user and distinguished from the tooth surface during application and while in place. The film gel is sufficiently strong and adherent enough to remain on the teeth for a period of time, for example up to 30 minutes to effect a whitening result and will resist the forces commonly applied by the lips and tongue. While the film is in place, the user is to refrain from mastication. The film can be removed as and when required, at will, by an employment of standard oral hygiene procedures such as brushing or by rinsing with an alcoholic mouthwash. While in place the film releases agents contained therein at a slow, relatively constant rate and in concentration sufficient effectively to effect stain removal from the teeth.

The whitening benefit imparted by the whitening gel of the present invention may be enhanced by brushing the teeth, before or after the application of the whitening gel, with a whitening toothpaste containing peroxide whitening agents or stain removing silica or alumina abrasives or a rinse composition having an alkaline pH as disclosed in U.S. Pat. No. 6,174,516.

The liquid whitening gel compositions of the present invention are prepared by adding and mixing the ingredients of the composition in a suitable vessel such as a stainless steel tank provided with a mixer. In the preparation of the liquid whitening composition, the ingredients are advantageously added to the mixer in the following order: solvent film forming agent, humectant and peroxide compound and any desired flavoring. The ingredients are then mixed to form a homogeneous dispersion/solution. Thereafter an opacifier such as polyethylene, polytetrafluoroethylene or titanium dioxide coated mica particles are added to the solution. The present invention is illustrated by the following example but is not to be limited thereby.

EXAMPLE

A liquid whitening gel base formula having a pH of 4.0 was prepared having the ingredients listed in Table I below:

TABLE I

Liquid Whitening Gel Base Formula

| Ingredient | % by Weight |
|---|---|
| Water | 10.07 |
| Carbopol 974 | 1.00 |
| 95% Ethyl alcohol | 34.8 |
| Glycerin | 5.00 |
| PEG 600 | 10.00 |
| PEG 2M | 14.00 |
| Hydrogen peroxide | 25.00 |
| 85% Phosphoric acid | 0.05 |
| Monobasic sodium phosphate | 0.05 |
| Total | 100.00 |

A series of liquid whitening gels was prepared in which the base formula of Table I was modified by either (1) 2 to 5% by weight a polyethylene (PE) powder having an average particle size of 6 to 8 microns; (2) 1 to 5% by weight of a polytetrafluoroethylene (PTFE) powder having particle size of 5 to 6 microns; (3) 0.8 to 2.5% by weight polypropylene powder having a particle size of 4 to 50 microns; (4) 2 to 5% by weight of the PE powder and 0.11 to 0.4% by weight of titanium dioxide powder having a particle size of 10 to 45 microns. The amounts of the polymer and inorganic titanium powders incorporated in the base formula are recorded in Tables II and III.

TABLE II

| | Liquid Whitening Gel Formula | | | | | | |
|---|---|---|---|---|---|---|---|
| | A (Wt. %) | B (Wt. %) | C (Wt. %) | D (Wt. %) | E (Wt. %) | F (Wt. %) | G (Wt. %) |
| Base Formula | 99.0 | 98.0 | 95.0 | 98.0 | 95.0 | 99.2 | 97.5 |
| + PE | — | — | — | 2.0 | 5.0 | — | — |
| + PTFE | 1.00 | 2.0 | 5.0 | — | — | — | — |
| + PP | — | — | — | — | — | 0.8 | 2.5 |

TABLE III

| Liquid Whitening Gel Formula | GA (Wt. %) | H (Wt. %) | I (Wt. %) | J (Wt. %) | K (Wt. %) | L (Wt. %) |
|---|---|---|---|---|---|---|
| Base Formula | 99.5 | 97.90 | 97.80 | 97.60 | 94.90 | 99.5 |
| + PE | — | 2.00 | 2.00 | 2.00 | 5.00 | — |
| + TiO$_2$ | — | 0.10 | 0.20 | 0.40 | 0.10 | — |
| + TiO$_2$ coated mica | 0.5 | — | — | — | — | — |

The shelf stability of the liquid whitening gel formulations A–K, packaged in plastic bottles was determined by the percent of active oxygen present in the whitening liquid after a two week exposure of plastic bottle packaged whitening compositions to a temperature of 120° F. (49° C.). Active oxygen analysis was performed using a standard iodometric titration method. The stability results are recorded in Table IV below.

TABLE IV

Active Oxygen Analysis

| Liquid Whitening Gel Formula | Initial | Final | % Loss* |
|---|---|---|---|
| A | 9.07 | 8.95 | None |
| B | 9.22 | 8.78 | None |
| C | 8.79 | 8.28 | 5.9% |
| D | 8.83 | 9.08 | None |
| E | 8.76 | 8.57 | None |
| F | 9.01 | 8.88 | None |
| G | 8.50 | 8.97 | None |
| GA | 9.05 | 8.95 | None |
| H | 8.97 | 9.13 | None |
| I | 9.10 | 8.85 | None |
| J | 8.63 | 8.70 | None |
| K | 8.61 | 8.41 | None |
| L | 9.05 | 8.95 | None |

*Loss of <5% is considered experimental error.

The active oxygen analysis results recorded in Table IV indicate that the liquid whitening gel of the present invention retained sufficient peroxide content to be an efficacious whitening composition even after two (2) weeks of storage at the elevated temperature of 120° F. (49° C.). Past experience with this temperature stability test indicated that when peroxide loss is less than 25% after two weeks at 120° F., a minimum shelf life of six (6) months can be expected.

Example II

Following in the procedure of Example I, a liquid whitening gel designated "Gel L" was prepared having the ingredients listed in Table V in which 0.38% by weight of titanium dioxide particles having a particle size of 10 to 45 microns was incorporated. Gel L packaged in plastic bottles after two (2) weeks at 120° F. active oxygen analysis indicated an oxygen loss of less than 5%.

TABLE V

| Liquid Gel Formula | Gel L (W %) |
|---|---|
| Carbomer | 1.00 |
| PEG 600 | 9.96 |
| BHT | 0.03 |
| Glycerin | 4.98 |
| Water | 17.00 |
| Ethyl alcohol | 34.67 |
| PEG 2M | 13.95 |
| H2O2 (35%) | 17.93 |
| Sodium Phosphate | 0.05 |
| Phosphoric acid | 0.05 |
| Titanium dioxide | 0.38 |

For purposes of comparison, the procedure of the Example II was repeated except the base formula was modified with 5% by weight $TiO_2$ designated "Gel M". After two (2) weeks at 120° F., active oxygen analysis indicated that Gel M had an unacceptable oxygen loss of 41.24%

For purposes of further comparison, a liquid whitening gel formula of the prior art (U.S. Pat. No. 5,425,953) designated Gel N, the ingredients of which are listed in Table VI, below. Gel N was modified with 0.19 and 0.38% by weight of titanium oxide particles. These gels designated Liquid Gel Formula O and P were also prepared using the ingredients listed in Table VI below.

TABLE VI

| Liquid Whitening Gel Formulation | N (Wt. %) | O (Wt. %) |
|---|---|---|
| Water | 28.95 | 29.27 |
| Ethanol | 50.50 | 51.80 |
| Hydroxypropyl cellulose | 12.45 | 12.45 |
| Carbamide peroxide | 8.00 | 6.00 |
| Calcium EDTA | 0.10 | 0.10 |
| Titanium dioxide | 0.00 | 0.38 |

The shelf stability of whitening gels N and O packaged in plastic bottles was determined as the percent peroxide recovered from the gels after a 2 week exposure at 120° F. (49° C.). Percent peroxide recovery was performed using standard iodometric titration method. The stability results are recorded in Table VII below.

TABLE VII

LIQUID WHITENING GEL STABILITY

| Liquid Whitening Gel Formula | Initial Wt. % $H_2O_2$ | Wt. % $H_2O_2$ After 2 Weeks at 120° F. | % Recovery of $H_2O_2$ |
|---|---|---|---|
| N | 7.89 | 6.00 | 76 |
| O | 5.54 | 0.67 | 12 |

What is claimed is:

1. A stable opaque liquid tooth whitening gel composition suitable for application to teeth in the oral cavity comprising a peroxide containing compound dispersed in an orally acceptable vehicle containing a solvent, a film forming agent a mixture of (A) about 5% to about 50% of poly (ethylene oxide), molecular weight from 100,000 to 4,000,000, and (B) from about 0.25% to about 1.5% by weight of a carbomer which is a cross-linked acrylic acid copolymer and an opacifier selected opacifying organic polymer particles, having an average particle size of about 0.5 microns to about 100 microns, selected form the group consisting of polyethylene, polypropylene, ethylene/propylene copolymer, polytetrafluoro-ethylene and polyhexafluoropropene, said polymeric, pacifying particles being incorporated at a concentration of about 1% to about 30% by weight in said liquid whitening gel having a particle size of about 0.5 to 100 microns.

2. The composition of claim 1 wherein the vehicle is comprised of water and a monohydric alcohol.

3. The composition of claim 1 wherein the peroxide containing compound is urea peroxide or hydrogen peroxide.

4. The composition of claim 1 wherein the peroxide containing compound is present in the composition at a concentration that will provide about 0.3 to about 12% by weight peroxide to the composition.

5. The composition of claim 1 wherein the concentration of the peroxide containing compound is present in the composition at a concentration that will provide about 1 to about 10% by weight peroxide to the composition.

6. The composition of claim 1 wherein the opacifier is an organic polymer having an average particle size in the range of 1 to about 100 microns.

7. The composition of claim 1 wherein the organic opacifier has a particle size of about 1 to about 20 microns.

8. The composition of claim 6 wherein the organic polymer is polyethylene.

9. The composition of claim 6 wherein the organic polymer is polypropylene.

10. The composition of claim 6 where the organic polymer is polytetrafluoroethylene.

11. The composition of claim 1 wherein the organic opacifier is present in the composition at a concentration of about 1 to about 10% by weight.

12. The method for whitening teeth which comprises:
(a) preparing a liquid gel tooth whitening composition of claim 1;
(b) painting the composition into contact with the teeth to be whitened;
(c) maintaining the composition in contact with the teeth to effect tooth whitening.

\* \* \* \* \*